United States Patent
Mittal et al.

(10) Patent No.: US 10,838,412 B2
(45) Date of Patent: Nov. 17, 2020

(54) HYBRID MACHINE LEARNING APPROACH TOWARDS OLEFINS PLANT OPTIMIZATION

(71) Applicant: SABIC Global Technologies B.V., Bergen op Zoom (NL)

(72) Inventors: Akash Mittal, Bangalore (IN); Abduljelil Iliyas, Riyadh (SA)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

(21) Appl. No.: 16/621,301

(22) PCT Filed: Jun. 8, 2018

(86) PCT No.: PCT/IB2018/054165
§ 371 (c)(1),
(2) Date: Dec. 11, 2019

(87) PCT Pub. No.: WO2018/229621
PCT Pub. Date: Dec. 20, 2018

(65) Prior Publication Data
US 2020/0096982 A1 Mar. 26, 2020

Related U.S. Application Data

(60) Provisional application No. 62/519,715, filed on Jun. 14, 2017.

(51) Int. Cl.
*G05B 19/418* (2006.01)
*C07C 4/04* (2006.01)
(Continued)

(52) U.S. Cl.
CPC .......... *G05B 19/41885* (2013.01); *C07C 4/04* (2013.01); *C10G 9/36* (2013.01);
(Continued)

(58) Field of Classification Search
CPC .......... G05B 19/41885; G05B 13/0265; G05B 2219/32287; C07C 4/04; C10G 9/36; C10G 9/14; C10G 11/00
See application file for complete search history.

(56) References Cited

U.S. PATENT DOCUMENTS

| 7,424,395 B2 | 9/2008 | Emigholz et al. ............ 702/182 |
| 8,019,593 B2 | 9/2011 | Weng et al. ...................... 704/9 |

(Continued)

FOREIGN PATENT DOCUMENTS

| CN | 103093069 B | 9/1916 |
| CN | 101414158 A | 4/2009 |

(Continued)

OTHER PUBLICATIONS

Alizadeh et al. "Modeling of Thermal Cracking Furnaces Via Exergy Analysis Using Hybrid Artificial Neural Network—Genetic Algorithm." *J. Heat Transfer* 138(4), 042801 (Jan. 20, 2016) (11 pages).

(Continued)

*Primary Examiner* — Ali Z Fadhel
(74) *Attorney, Agent, or Firm* — Norton Rose Fulbright US LLP

(57) ABSTRACT

The present disclosure describes systems, methods, and computer readable media that provide a hybrid approach that uses machine learning techniques and phenomenological reactor models for optimization of steam cracker units. While the phenomenological model allows capturing the physics of a steam cracker using molecular kinetics, the machine learning methods fill the gap between the phenomenological models and more detailed radical kinetics based steam cracker models. Also, machine learning based models can capture actual plant information and provide insight into the variation between the models and plant running conditions. The proposed methodology shows better interpolation (Continued)

and extrapolation capabilities as compared to stand-alone machine learning methods. Also, compared to detailed radical kinetics based models, the approach utilized in embodiments requires much less computational time in order to carry out whole plant-wide optimization or can be used for planning/scheduling purposes.

20 Claims, 3 Drawing Sheets

(51) Int. Cl.
*C10G 9/36* (2006.01)
*G05B 13/02* (2006.01)
*C10G 11/00* (2006.01)
*C10G 9/14* (2006.01)

(52) U.S. Cl.
CPC ........... *G05B 13/0265* (2013.01); *C10G 9/14* (2013.01); *C10G 11/00* (2013.01); *G05B 2219/32287* (2013.01)

(56) References Cited

U.S. PATENT DOCUMENTS

| | | | |
|---|---|---|---|
| 9,261,865 | B2 | 2/2016 | Morrison et al. |
| 9,471,884 | B2 | 10/2016 | Hamann et al. |
| 2008/0128325 | A1* | 6/2008 | Khan ................. B01J 23/10 208/67 |
| 2012/0095808 | A1* | 4/2012 | Kattapuram ..... G06Q 10/06375 705/7.37 |
| 2012/0193269 | A1 | 8/2012 | Taha et al. ................. 208/95 |
| 2014/0365409 | A1 | 12/2014 | Burch et al. .................. 706/12 |
| 2016/0078368 | A1 | 3/2016 | Kakhandiki et al. ........... 706/12 |
| 2017/0101586 | A1* | 4/2017 | Iliyas ....................... C10G 9/36 |

FOREIGN PATENT DOCUMENTS

| | | |
|---|---|---|
| CN | 102213949 B | 12/2014 |
| CN | 103087753 B | 12/2014 |
| CN | 103087752 B | 4/2015 |
| CN | 105184403 A | 12/2015 |
| FR | 2906481 A1 | 4/2008 |
| WO | WO2008057546 A2 | 5/2008 |
| WO | WO2015106372 A1 | 7/2015 |

OTHER PUBLICATIONS

Bellos et al. "Modelling of the performance of industrial HDS reactors using a hybrid neural network approach." *Chemical Engineering and Processing*, 2005, 44:505-515.

Dorn et al. "Combining Machine Learning and Optimization Techniques to Determine 3-D Structures of Polypeptides." *IJCAI Proceedings—International Joint Conference on Artificial Intelligence*. vol. 22. No. 3. 2011.

Huiyuan Shi et al. "Nonlinear Adaptive Predictive Functional Control Based on the Takagi-Sugeno Model for Average Cracking Outlet Temperature of the Ethylene Cracking Furnace." Ind. Eng. Chem. Res., vol. 54, No. 6, 2015, 1849-1860.

International Search Report and Written Opinion from PCT/IB2018/054165 dated Aug. 17, 2018, 11 pages.

Nasiri et al. "A Hybrid Neural Network and Traditional Approach for Forecasting Lumpy Demand." *Proceedings of World Academy of Science: Engineering & Technology*, Jun. 2008, vol. 42, p. 384.

Oliveira, R. "Combining first principles modelling and artificial neural networks: a general framework." *Computers & Chemical Engineering*, vol. 28, Issue 5, May 15, 2004, pp. 755-766.

Orru et al. "An Investigation on the Failure Risks in a Steam Cracking Plant." ASME. 8th Biennial Conference on Engineering Systems Design and Analysis, vol. 2: Automotive Systems, Bioengineering and Biomedical Technology, Fluids Engineering, Maintenance Engineering and Non-Destructive Evaluation, and Nanotechnology, Torino, Italy, Jul. 4-7, 2006, 9 pages.

Shaoduan O., Luke E.K. Achenie , "A hybrid neural network model for PEM fuel cells", Journal of Power Sources, vol. 140, Issue 2, Feb. 2, 2005, pp. 319-330.

* cited by examiner

HYBRID MACHINE LEARNING APPROACH TOWARDS OLEFINS PLANT OPTIMIZATION

CROSS REFERENCE TO RELATED APPLICATIONS

This application is a national phase application under 35 U.S.C. § 371 of International Application No. PCT/IB2018/054165 filed Jun. 8, 2018, which claims priority to U.S. Provisional Patent Application No. 62/519,715 filed Jun. 14, 2017. The entire contents of each of the above-referenced disclosures is specifically incorporated by reference herein without disclaimer.

FIELD OF INVENTION

The present invention generally relates to cracking of hydrocarbons, and more particularly to modelling techniques providing improved olefin yield predictions for a cracking process performed by a cracking unit and/or an olefin plant and for determining operating conditions for the cracking unit and/or the olefin plant.

BACKGROUND OF THE INVENTION

Distilling crude oil to produce products such as butane (or lighter hydrocarbons), straight run gasoline, naphtha, kerosene, light gas oil, heavy gas oil, and straight run residue is simply separating the crude oil into its various constituents. Thus, under set processing conditions, the relative proportions of the products produced from a particular type of crude oil will roughly remain constant. However, based on market demands, it may be more economical to be able to increase the proportion of one or more of the products at the expense of other products. For example, when the demand for gasoline is high, it may be more economical to produce more gasoline than heavy gas oil. Thus, processes have been developed to convert one type of distilled product to another. One such process is catalytic cracking, in which longer and heavier hydrocarbon molecules are contacted with a catalyst at high temperatures and pressures to break them into lighter and shorter hydrocarbon molecules. Although processes such as cracking have been developed to transform longer and heavier hydrocarbon molecules into lighter and short hydrocarbon molecules, cracking of hydrocarbons is a complex process and, when trying to configure the process to yield a lighter or shorter hydrocarbon(s) of interest, it is often difficult to predict what the actual yield of the of the hydrocarbon(s) of interest will be or to determine a configuration of a plant where the cracking process is to take place to achieve a desired quantity of the hydrocarbon(s) of interest.

BRIEF SUMMARY OF THE INVENTION

A method has been discovered for improving the accuracy of olefin yields resulting from a cracking process and for establishing operating conditions for a cracking unit and/or an olefin plant to produce the olefins. The proposed method may provide feed flow, composition data and operating conditions as inputs to a phenomenological model and to a radical kinetics based model. An output yield pattern for the phenomenological model and an output yield pattern for radical kinetics based model may be generated. A difference between the two output yield patterns may be determined, which can then be used as an input for training a machine learning model. The feed flow and/or composition data and the operating conditions may then be provided to the phenomenological model and a machine learning tool. The phenomenological model may utilize the input data to derive a predicted yield pattern. The machine learning tool may be configured to predict a yield, which may be added to the output from the phenomenological based model to generate a corrected yield, which may more accurately reflect a final yield of olefins that may be obtained by executing a cracking process at the olefin plant.

Embodiments of the invention include a method of producing olefins by an olefins plant, as well as systems and computer-readable storage media configured to execute operations to implement the method via one or more processors. The method may include running a phenomenological model, with input including operating conditions for a cracking unit, to generate an output of a first olefin yield of the cracking unit, where the phenomenological model is based on molecular kinetics. The method may further include running a free radical kinetics based model, with input including the operating conditions for the cracking unit, to generate an output of a second olefin yield of the cracking unit. The method may further include determining the difference between the first olefin yield of the cracking unit and the second olefin yield of the cracking unit (E), and running a machine learning model, with input including the operating conditions for the cracking unit, to generate a predicted E. The method may further include adding the predicted E to the first olefin yield to obtain a corrected olefin yield, establishing new operating conditions for the cracking unit and/or the olefin plant based at least on the corrected olefin yield, and producing the olefins by the olefin plant while operating under the new operating conditions.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention, at least twenty embodiments are now described. Embodiment 1 is a method of producing olefins by an olefins plant. The method includes the steps of running a phenomenological model, with input including operating conditions for a cracking unit, to generate an output of a first olefin yield of the cracking unit, the phenomenological model based on molecular kinetics; running a free radical kinetics based model, with input including the operating conditions for the cracking unit, to generate an output of a second olefin yield of the cracking unit; determining the difference between the first olefin yield of the cracking unit and the second olefin yield of the cracking unit (E); running a machine learning model, with input including the operating conditions for the cracking unit, to generate a predicted E; adding the predicted E to the first olefin yield to obtain a corrected olefin yield; establishing new operating conditions for the cracking unit and/or the olefin plant based at least on the corrected olefin yield; and producing the olefins by the olefin plant while operating under the new operating conditions. Embodiment 2 is the method of embodiment 1, wherein the producing the olefins by the olefin plant while operating under the new operating conditions include steam cracking. Embodiment 3. Is the method of any of embodiments 1 and 2, wherein the olefins include ethylene. Embodiment 4 is the method of any of embodiments 1 to 3, wherein the method includes generating training data based on the phenomenological model and the free radical kinetics based model. Embodiment 5 is the method of any of embodiments 1 to 4, wherein the method includes receiving plant data, wherein the plant data is utilized to run the free radical kinetics based model. Embodiment 6 is the method of embodiment 5, wherein the plant data includes data representative of actual operating conditions and data representative of actual olefin yields observed based on the actual operating conditions, the data representative of the actual operating conditions including data associated with a feed flow rate, a feed flow composition, a temperature, and a pressure utilized to produce the olefins. Embodiment 7 is the method of any of embodiments 1 to 6, wherein the method includes utilizing stochastic tools, wherein the stochastic tools include at least Kalman filters.

Embodiment 8 is a non-transitory computer-readable storage medium storing instructions that, when executed by one or more processors, cause the one or more processors to perform operations for analyzing, controlling, or both, production of olefins by an olefins plant, the operations including the steps of running a phenomenological model, with input including operating conditions for a cracking unit, to generate an output of a first olefin yield of the cracking unit, the phenomenological model based on molecular kinetics, the operating conditions including conditions selected from the list consisting of: feed flow rate, feed flow composition, temperature, pressure, and combinations thereof; running a free radical kinetics based model, with input including the operating conditions for the cracking unit, to generate an output of a second olefin yield of the cracking unit; determining the difference between the first olefin yield of the cracking unit and the second olefin yield of the cracking unit (E); running a machine learning model, with input including the operating conditions for the cracking unit, to generate a predicted E; adding the predicted E to the first olefin yield to obtain a corrected olefin yield; establishing new operating conditions for the cracking unit and/or the olefin plant based at least on the corrected olefin yield; and producing the olefins by the olefin plant while operating under the new operating conditions. Embodiment 9 is the non-transitory computer-readable storage medium of embodiment 8, wherein the producing the olefins by the olefin plant while operating under the new operating conditions includes steam cracking. Embodiment 10 is the non-transitory computer-readable storage medium of any of embodiments 8 and 9, wherein the olefins include ethylene. Embodiment 11 is the non-transitory computer-readable storage medium of any of embodiments 8 to 10, wherein the operations include generating training data based on the phenomenological model and the free radical kinetics based model. Embodiment 12 is the non-transitory computer-readable storage medium of any of embodiments 8 to 11, wherein the operations include receiving plant data, wherein the plant data is utilized to run the free radical kinetics based model. Embodiment 13 is the non-transitory computer-readable storage medium of embodiment 12, wherein the plant data includes data representative of actual operating conditions and data representative of actual olefin yields observed based on the actual operating conditions, the data representative of the actual operating conditions including data associated with a feed flow rate, a feed flow composition, a temperature, and a pressure utilized to produce the olefins. Embodiment 14 is the non-transitory computer-readable storage medium of any of embodiments 8 to 13, wherein the operations include utilizing stochastic tools, wherein the stochastic tools include at least Kalman filters.

Embodiment 15 is a system for producing olefins at an olefins plant. The system includes at least one processor configured to: run a phenomenological model, with input including operating conditions for a cracking unit, to generate an output of a first olefin yield of the cracking unit, the phenomenological model based on molecular kinetics, the operating conditions including conditions selected from the list consisting of: feed flow rate, feed flow composition, temperature, pressure, and combinations thereof; run a free radical kinetics based model, with input including the operating conditions for the cracking unit, to generate an output of a second olefin yield of the cracking unit; determine the difference between the first olefin yield of the cracking unit and the second olefin yield of the cracking unit (E); run a machine learning model, with input including the operating conditions for the cracking unit, to generate a predicted E, wherein the running of the machine learning model includes training the machine learning model with training data including a predetermined range of operating conditions; add the predicted E to the first olefin yield to obtain a corrected olefin yield; establish new operating conditions for the cracking unit and/or the olefin plant based at least on the corrected olefin yield; and initiate operations to produce the olefins by the olefin plant while operating under the new operating conditions; and a memory coupled to the at least one processor. Embodiment 16 is the system of embodiment 15, wherein the production of the olefins by the olefin plant while operating under the new operating conditions includes steam cracking. Embodiment 17 is the system of any of embodiments 15 and 16, wherein the olefins include ethylene. Embodiment 18 is the system of any of embodiments 15 to 17, wherein the at least one processor is further configured to generate training data based on the phenomenological model and the free radical kinetics based model. Embodiment 19 is the system of any of embodiments 15 to 18, wherein the at least one processor is further configured to receive plant data and utilize the plan data to run the free radical kinetics based model. Embodiment 20 is the system of embodiment 19, wherein the plant data includes data representative of actual operating conditions and data representative of actual olefin yields observed based on the actual operating conditions, the data representative of the actual operating conditions includes data associated with a feed flow rate, a feed flow composition, a temperature, and a pressure utilized to produce the olefins.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Figure 1:
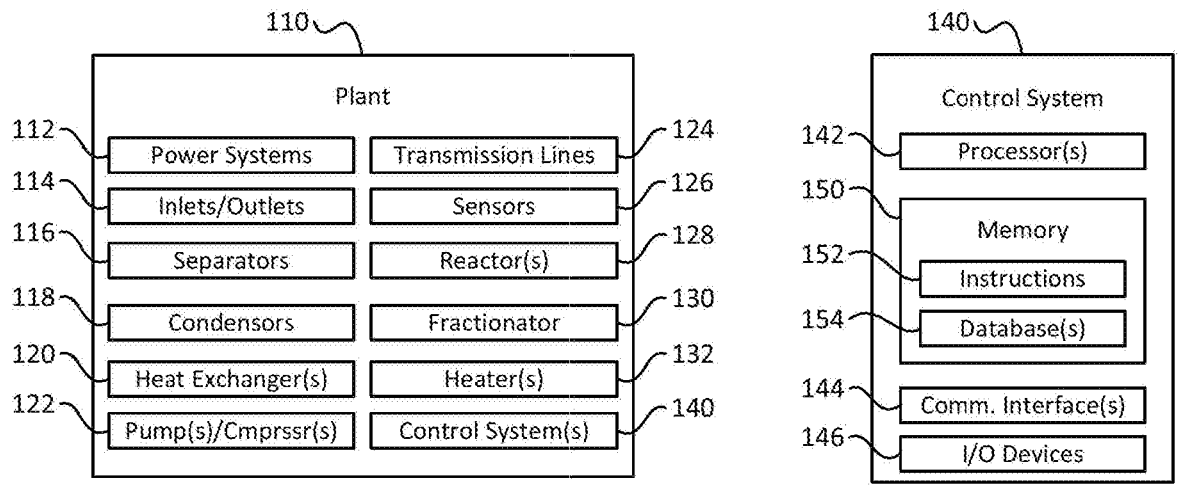
FIG. 1 is a block diagram of an olefin plant configured according to embodiments.

A method has been discovered for improving the accuracy of olefin yield predictions for a cracking process carried out by an olefin plant/production facility. Referring to FIG. 1, a block diagram of an olefin plant configured according to embodiments is shown as an olefin plant 100. As shown in FIG. 1, the olefin plant 100 may include a power system 102, one or more inlets and/or outlets 104, one or more separators 106, one or more condensers 108, one or more heat exchangers 110, one or more pumps and/or compressors 112, one or more transmission lines 114, one or more sensors 116, one or more reactors 118, one or more fractionators 120, one or more heaters 122, and a control system 130.

The power system 102 may include power generation and distribution components. In embodiments, the power generation components of the power system 102 may include one or more generators and/or battery systems configured to provide electricity to one or more other components and/or systems of the olefin plant 100. In embodiments, the power distribution components may include power lines configured to distribute the power generated by the power generation components and/or power received from an external source (e.g., an external power grid) to one or more components and/or systems of the olefin plant 100.

The one or more inlets and/or outlets 104 may include one or more inlets configured to receive a feedstock (e.g., a flow of hydrocarbons, etc.) into the olefin plant 100, and may include one or more inlets configured to receive a portion of the feedstock, or a portion of the processed feedstock into one or more particular components, such as the one or more transmission lines 114, the one or more reactors 118, the one or more fractionators 120, and the like, during the production of olefins at the olefin plant 100. It is noted that in embodiments, the feedstock may include a raw (e.g., unprocessed) flow of hydrocarbons, such as a flow of heavy and/or long chain hydrocarbons or hydrocarbon molecules. In embodiments, the olefin plant 100 may also receive other types of materials in addition to the raw flow of hydrocarbons. The olefin plant 100 may receive water, which may be used for cooling or other purposes, such as generating steam which may be used to provide heat and/or generate power, and/or may receive other hydrocarbons, such as natural gas or methane, which may be used to provide heat and/or generate power. The one or more inlets/outlets 104 may further include one or more outlets configured to output one or more olefins produced by the olefin plant 100. In embodiments, the olefins may be output to one or more storage containers/facilities, pipelines, and the like. In embodiments, the one or more transmission lines 114 may facilitate transport of the feedstock and other materials utilized by the olefin plant 100 to various components of the olefin plant 100 to facilitate production of the one or more olefins.

In embodiments, the one or more separators 106, the one or more condensers 108, the one or more heat exchangers 110, the one or more pumps and/or compressors 112, the one or more reactors 118, the one or more fractionators 120, and the one or more heaters 122 may be configured to process the feedstock of raw hydrocarbons and/or hydrocarbon molecules to produce the one or more olefins. In embodiments, one or more of these components may be configured to facilitate a cracking process, which, as explained above, is a process to transform heavy and/or long hydrocarbon molecules into lighter and/or shorter hydrocarbon molecules. In embodiments, the cracking process may include steam cracking and/or thermal cracking. The one or more sensors 116 may include temperature sensors configured to provide information representative of temperatures observed at various points and/or components of the olefin plant 100, pressure sensors configured to provide information representative of various pressures measured at various points and/or components of a cracking unit and/or the olefin plant 100, flow sensors configured to provide information representative of various rates of flow observed at various points and/or components of the olefin plant 100, and other types of sensors (e.g., sensors to capture/provide information associated with an ambient environment associated with the olefin plant 100, etc.).

As shown in FIG. 1, the control system 130 may include one or more processors 132, one or more communication interfaces 134, one or more input/output devices 136, and a memory 150. The memory 150 may include one or more random access memory (RAM) devices, read only memory (ROM) devices, one or more hard disk drives (HDDs), flash memory devices, solid state drives (SSDs), network attached storage (NAS) devices, other devices configured to store data in a persistent or non-persistent state, or a combination of different memory devices.

In embodiments, the memory 150 may store instructions 152 which, when executed by the one or more processors 132, cause the one or more processors 132 to perform operations for producing olefins at the olefins plant 100. In an embodiment, the instructions 152 may correspond to an application, a script, an applet, or other programmed functionality that may be executed by the one or more processors 132 to facilitate analysis and production of olefins by the olefin plant. In embodiments, the application corresponding to the instructions 152 may be a stand-alone application, a web-based application, and the like. The instructions 152 may be configured to provide one or more graphical user interfaces (GUIs) that may be utilized to provide information associated with the olefin plant to a user (e.g., an operator of the olefin plant 100). For example, a GUI may be configured to present, to a user, information associated with predicted olefin yields from performing a cracking process on a feedstock of raw hydrocarbons having particular properties. In embodiments, the one or more GUIs may also be configured to receive information from the user. For example, a GUI may be configured to receive, as input, information indicating one or more properties of the feedstock of raw hydrocarbons. In embodiments, the one or more GUIs may further be configured to present information associated with a configuration of the olefin plant 100. For example, the information associated with the configuration the olefin plant 100 may correspond to a configuration of one or more components of the olefin plant 100 to produce the olefins.

In embodiments, the control system 130 may be communicatively coupled to one or more components of the olefin plant 100, such as the one or more sensors 116 and other components of the olefin plant 100, and may provide control messages to at least one of the one or more sensors 116 and the other components. In embodiments, the control messages may identify one or more operating conditions for the olefin plant 100. For example, a control message sent to one of the one or more cracking unit reactors may identify one or more operating conditions to configure the reactor for production of olefins. As described in more detail below, the one or more operating conditions may be utilized to configure the olefin plant 100 (in particular, the cracking unit) to produce one or more olefins of interest. In embodiments, the one or more operating conditions may be configured to cause increases and/or decreases in the volume or quantity of each type of olefin produced by the olefin plant 100. This enables the olefin plant 100 to be configured to produce particular olefins in particular quantities, which may facilitate production of larger quantities of olefins of high value.

Additionally, one or more databases 154 may be stored at the memory 150. In embodiments, the one or more databases 154 may store historical information associated with actual operating conditions of the olefin plant 100 during execution of a cracking process), such as temperatures at which particular components such as the cracking unit or the one or more heaters 132 were operating at during the cracking process, catalysts utilized during the cracking process, temperature differentials at the one or more heat exchangers 120 during the cracking process, pressures utilized to produce the olefins during the cracking process, a feed flow rate indicating a flow rate for the feedstock into the olefin plant 100 and/or flow rates with respect to various components of the olefin plant 100, a feed flow composition including data representative of the properties of the feedstock provided to the olefin plant, and the like. In embodiments, the one or more databases 154 may further store information associated with actual olefin yields for various executions of the cracking process (e.g., for particular periods of time, different compositions of feedstock, or a combination thereof).

As briefly explained above, the olefin plant 100 may be configured to perform a cracking process to transform a feedstock of raw hydrocarbons into one or more olefins. In embodiments, the cracking process may correspond to a steam cracking process. In some embodiments, the cracking process may correspond to a thermal cracking process. In still other embodiments, the olefin plant may perform a combination of steam cracking and thermal cracking processes. Exemplary aspects for producing olefins by an olefin plant, such as the olefin plant 100, are described in more detail below.

The cracking reaction is governed by free radical mechanism, and detailed simulation typically requires more than two thousand (2000) reactions and components. This makes simulation of the cracking process using radical kinetic based models computationally expensive and prohibits the use of these models directly under an optimization framework, especially for planning/scheduling purpose or for whole plant optimization. Models based on a molecular kinetic mechanism (referred to as phenomenological models here) may be used for whole plant optimization and other purposes. These models utilize a simplified or lumped approach which addresses the physics of the problem, but lacks the ability to predict the exact product distribution. These types of models are not very computationally expensive and may be used for whole plant modeling. However, the product distribution is limited to the lumps used, which may limit the ability to obtain very detailed analysis from such models.

According to embodiments, machine learning techniques, such as artificial neural networks, may be used to estimate or approximate functions that can depend on a large number of inputs and are generally complex. In the case of a steam cracker, various inputs like feed flow composition, operating parameters like severity, pressure and coking conditions may impact the yield pattern. These models may be configured with sets of adaptive weights (i.e., numerical parameters) that may be tuned by a learning algorithm. In order to carry out learning for these models, embodiments utilize a large set of training data. In a stand-alone machine learning technique, the process inputs and corresponding outputs from a detailed model containing radical kinetics or plant data may be used for training purposes. Existing machine learning tools address the computational requirement issues, but are limited by their interpolation/extrapolation capabilities. In particular, they do not address the physics behind the cracking mechanism directly, and any slight change in the feedstock and/or operating conditions outside of the learning regime will produce vague results.

Figure 2:
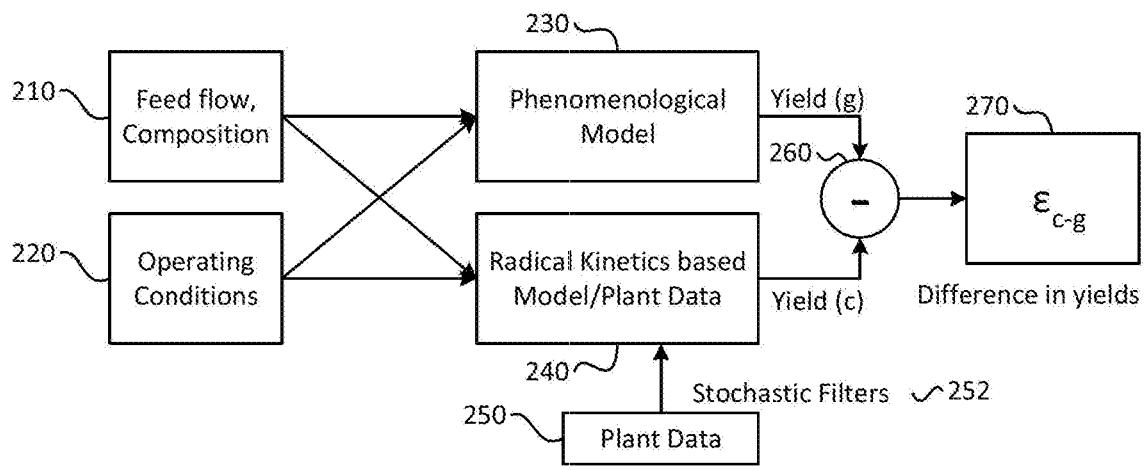
FIG. 2 is a block diagram of a first modelling technique for generating input data for a machine learning tool according to embodiments.

Embodiments of the present invention propose a hybrid approach that uses machine learning techniques and phenomenological reactor models based on molecular kinetic models. For example, and referring to FIG. 2, a block diagram of a first modelling technique for generating input data for a machine learning tool according to embodiments is shown. As shown in FIG. 2, feed flow and composition data 210 and operating conditions 220 may be provided as inputs to a phenomenological model 230 and to a radical kinetics based model 240. In embodiments, the feed flow and composition data 210 may include information that indicates one or more types of hydrocarbon molecules present in the feedstock, a flow rate for the feedstock, and other parameters. In embodiments, the operating conditions 220 may include information associated with a configuration of the olefin facility, such as temperatures, pressures, and the like of one or more components of the olefin facility. In embodiments, plant data 250 may be provided as an input to the radical kinetics based model 240. The plant data 250 may include information representative of actual operating conditions and data representative of actual olefin yields observed based on the actual operating conditions. The information representative of the actual operating conditions may include data associated with a feed flow rate, a feed flow composition, a temperature, and a pressure utilized to produce the olefins. In embodiments, stochastic tools, such as Kalman filters, may also be utilized. Such tools may enable assessment, by the radical kinetics based model 240, of a relevant set of data only.

In embodiments, the phenomenological model 230 may use molecular kinetics and may be computationally more effective as compared to the radical kinetics based model 240 (e.g., due to lumping). As shown in FIG. 2, using the same inputs, an output yield pattern for the phenomenological model (Yield (g)) and an output yield pattern for radical kinetics based model (Yield (c)) may be generated. Difference logic 260 may be utilized to determine a difference between the two output yield patterns ($\varepsilon_{c-g}$). As described in more detail below with reference to FIG. 3, the difference ($\varepsilon_{c-g}$) may then be used as an input for training a machine learning model.

Figure 3:
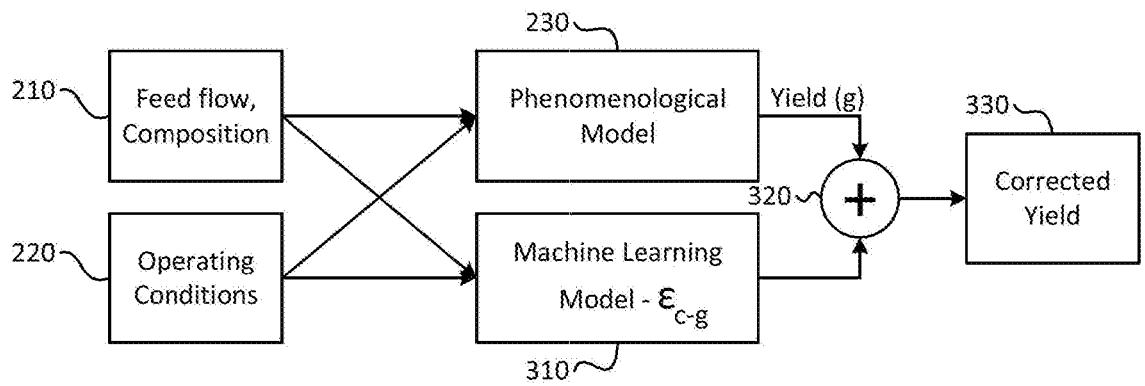
FIG. 3 is a block diagram illustrating a second modelling technique that utilizes a machine learning technique to predict a yield of one or more olefins using a cracking process according to embodiments.

In order to produce enough training and validation data for a machine learning tool, a Design of Experiments (DOE) configured to cover the given range of input conditions may be used. DOE methods, such as space filling design, may be used to generate the set of input conditions, which may then be used to generate the training dataset by running both phenomenological and detailed radical kinetics based model. The training dataset may be used to train a machine learning tool (or model). In embodiments, the trained machine learning tool is utilized as an additive to the phenomenological model based yield prediction to generate a corrected yield. For example, and referring to FIG. 3, a block diagram illustrating a second modelling technique that utilizes a machine learning technique to predict a yield of one or more olefins using a cracking process according to embodiments is shown. As shown in FIG. 3, the feed flow and/or composition data 210 and the operating conditions 220 may be provided to the phenomenological model 230 and a machine learning tool 310. As described above with reference to FIG. 2, the phenomenological model 230 may utilize the input data to derive a predicted Yield pattern (Yield (g)). The machine learning tool may be configured to predict a Yield ($\varepsilon$), which may be added to the output from the phenomenological based model 230 using additive logic 320 to generate a corrected Yield of olefins 330. The corrected Yield of olefins 330 may more accurately reflect a final Yield of olefins that may be obtained by executing a cracking process at the olefin plant.

As both phenomenological model 230 and machine learning model(s) 310 are computationally effective, the overall result represents a robust output generated within the time required for optimization or planning/scheduling purposes. Also, this overcomes the limitation of the stand-alone machine learning models which lack the extrapolation capabilities. For example, in embodiments where the input data set is not within the training dataset of the machine learning tool 310, a prediction of the Yield may be based the phenomenological model 230, making the overall process more robust.

The proposed methodology of embodiments shows better interpolation and extrapolation capabilities as compared to stand-alone machine learning methods. Also, compared to detailed radical kinetics based models, the approach of embodiments has less computational requirements for carrying out whole plant-wide optimization and can be used for planning/scheduling purpose. For example, based on the corrected Yield 330, new operating conditions for a cracking unit and/or the olefin plant may be determined, where the new operating conditions configured the cracking unit and/or olefin plant to achieve the corrected Yield 330.

Figure 7:
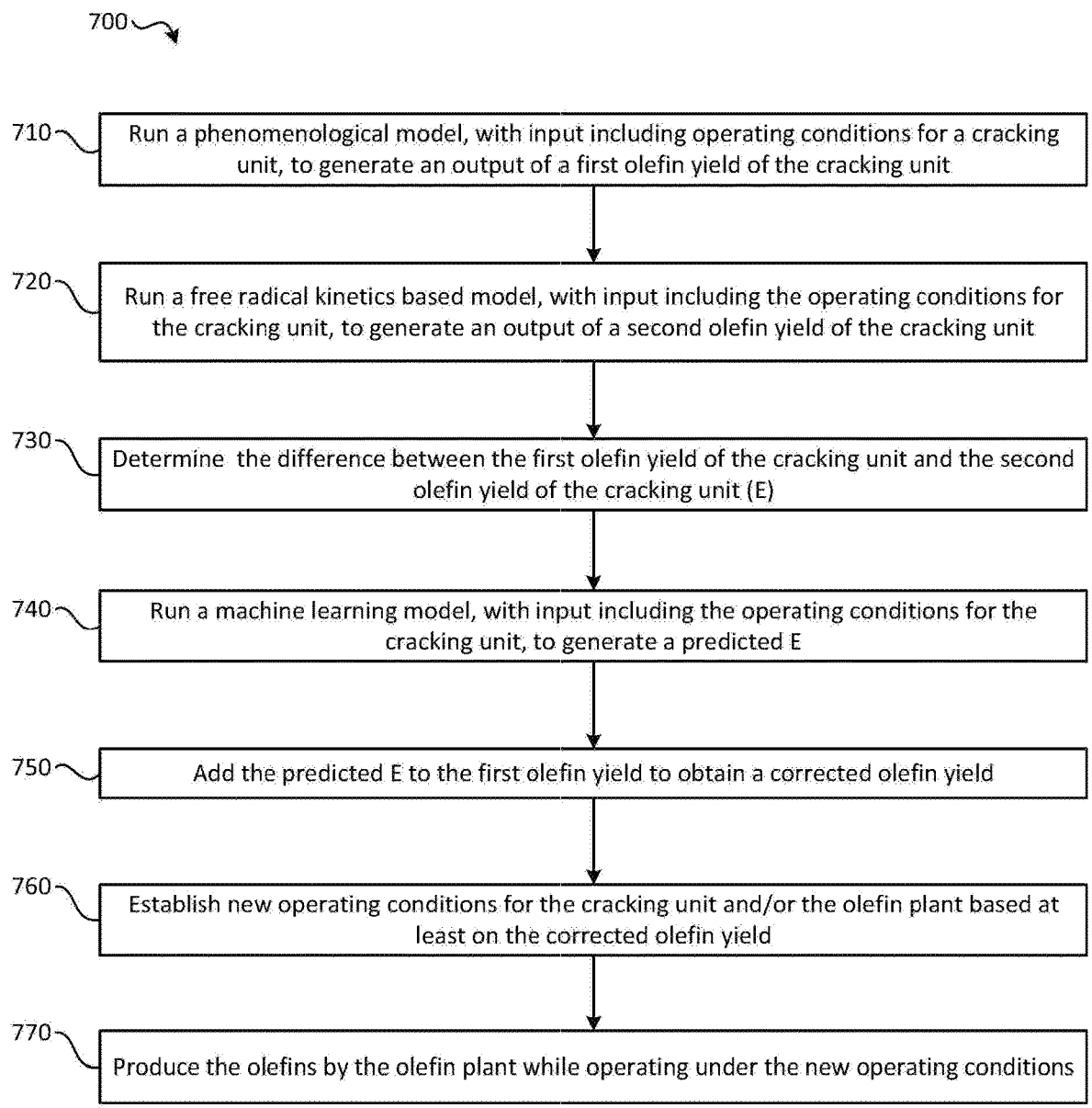
FIG. 7 is a flow diagram illustrating an exemplary method for producing olefins at an olefins plant according to embodiments.

Referring to FIG. 7, a flow diagram illustrating an exemplary method for producing olefins at an olefins plant according to embodiments is shown as a method 700. In embodiments, the method 700 may be stored as instructions (e.g., the instructions 152 of FIG. 1) that, when executed by one or more processors (e.g., the one or more processors 142), cause the one or more processors to perform operations for producing olefins by an olefins plant, such as the olefins plant 100 of FIG. 1. In embodiments, the instructions may provide one or more GUIs configured to receive one or more inputs, such as feedstock composition data, that may be utilized for configuring olefin plant 100 to produce the olefins.

At 710, the method 700 includes running a phenomenological model. In embodiments, the phenomenological model may correspond to the phenomenological model 230 of FIGS. 2 and 3, and may be run with inputs that may include operating conditions for a cracking unit, and may generate an output of a first olefin yield of the cracking unit. In embodiments, the phenomenological model may be based on molecular kinetics. In embodiments, the cracking unit may comprise one or more of the components of the olefin plant 100 of FIG. 1.

At 720, the method 700 includes running a free radical kinetics based model. In embodiments, the free radical kinetics based model may be the free radical kinetics based model 240 of FIG. 2. In embodiments, the free radical kinetics based model may be run with input including one or more operating conditions for the cracking unit, and may generate an output of a second olefin yield of the cracking unit. In embodiments, the method 700 may include receiving plant data, where the plant data is utilized to run the free radical kinetics based model, as described above with respect to FIG. 2. In embodiments, the plant data may include data representative of actual operating conditions and data representative of actual olefin yields observed based on the actual operating conditions, the data representative of the actual operating conditions comprising data associated with a feed flow rate, a feed flow composition, a temperature, and a pressure utilized to produce the olefins. In embodiments, this information may be obtained from a database, such as the database 154 of FIG. 1. In embodiments, stochastic tools may be utilized with respect to the running of the free radical kinetics based model. The stochastic tools may include at least Kalman filters.

At 730, the method 700 includes determining a difference between the first olefin yield of the cracking unit and the second olefin yield of the cracking unit (E), and at 740, running a machine learning model, with input including the operating conditions for the cracking unit, to generate a predicted E. In embodiments, the difference between the first olefin yield and the second olefin yield (E) may correspond to difference 270 of FIG. 2 and may be determined by difference logic 260 of FIG. 2, and the machine learning model may be the machine learning model 310 of FIG. 3.

At 750, the method 700 includes adding the predicted E to the first olefin yield to obtain a corrected olefin yield. In embodiments, the corrected olefin yield may correspond to the corrected olefin yield 330 of FIG. 3 and may be obtained using additive logic 320 of FIG. 3. At 760, the method 700 includes establishing new operating conditions for the cracking unit and/or the olefin plant based at least on the corrected olefin yield. In embodiments, the new operating conditions may correspond to a configuration of one or more components of the olefin plant, such as an operating temperature, pressure, feedstock flow rate, etc. of a cracking unit and/or the olefin plant. In embodiments, implementation of the new operating conditions may require reconfiguration or alteration of one or more settings of the olefin plant components, such as to modify a temperature of steam used in a steam cracking process. Such a modification may require a heater to be controlled to increase or decrease its heat output, where the heater is used to produce the steam utilized by a steam cracking process. Additional modifications to achieve the new operating conditions may include increasing or decreasing the flow rate of the feedstock at various points within the olefin plant, adjusting a pressure utilized by one or more components of the olefin plant, such as a condenser, which may in turn require modification of a load of a compressor, other modifications, and the like.

In embodiments, one or more GUIs may be provided to show the corrected olefin yield and/or the one or more new operating conditions for the olefin plant. In embodiments, a user or plant operator may utilize the GUIs to confirm the new operating conditions for the olefin plant, and, once the new operating conditions have been confirmed, the olefin plant may configured to operate under the new operating conditions. Requiring confirmation of the new operating conditions prior to implementing them may improve the safety of the olefin plant. In embodiments, the method 700 may be performed by a control system (e.g., the control system 130) of the olefin plant, and reconfiguration of the olefin plant may be initiated by the control system upon detecting confirmation of the new operating conditions. For example, once confirmed, the control system may exchange control messages with one or more components of the olefin plant to reconfigure the one or more components to operate under the new operating conditions, such as to control a valve to increase or decrease a flow rate, or modification of other settings/adjustments to configure one or more components of the olefin plant to operate in accordance with new operating conditions.

In other embodiments, reconfiguration of the olefin plant to operate under the new operating conditions may be performed manually as part of a period upkeep for the olefin plant. For example, a ratio of heavy/long hydrocarbons to shorter/lighter hydrocarbons present in feedstock is often not uniform over time (e.g., some time periods the feedstock may include a higher composition of heavy or long hydrocarbons while in other time periods the feedstock may include a higher composition of lighter/shorter hydrocarbons). Because of this variance, operating conditions and feedstock properties utilized by the olefin plant may be periodically (e.g., every few minutes, hour(s), days, etc.) monitored so that the olefin plant can be configured to operate at optimum efficiency and/or in a manner that is compatible with properties of the feedstock being received at the olefin plant. This periodic adjusting of the operating conditions of the olefin plant may improve the safety of the olefin plant, and may result in better yields of olefins being obtained. To facilitate the periodic adjustments, the control system may distribute messages to one or more persons responsible for configuring the various components of the olefin plant. Upon receiving the messages from the control system, the one or more persons may traverse the olefin plant and manually configure each of the one or more components of the olefin plant to operate in accordance with the new operating conditions, such as to adjust one or more valves to control the flow rate of the feedstock through the olefin plant, or other modifications. Once the olefin plant has been configured in accordance with the new operating conditions, the method 700 includes, at 770, producing the olefins by the olefin plant while operating under the new operating conditions.

In embodiments, the olefins produced by the olefin plant may include ethylene, propylene, butene, butadiene, benzene, or a combination thereof. In embodiments, the olefin plant may be configured to produce other products during processing of the feedstock to produce the olefins. However, such other products may not be affected or may be minimally affected by the new configuration of the olefin plant (e.g., because the other products are produced from the feedstock prior to, or after the olefins are produced). In embodiments, the method may also include generating training data based on the phenomenological model and the free radical kinetics based model, as described in more detail above.

In embodiments, the time for carrying out a simulation according to the method 700 may be less than one fifth ($\frac{1}{5}^{th}$) the time to carry out a simulation using the radical kinetics based model of the method only. Additionally, in embodiments, the time for carrying out plant optimization according to the method 700 may require one hundredth ($\frac{1}{100}^{th}$) of the time required to carry out a simulation using the radical kinetics based model of the method only. Thus, the method 700 of embodiments may result in significant time savings for performing simulations for olefin plant production and for performing whole plant optimization.

EXAMPLES

As part of the disclosure of the present invention, specific examples are included below. The examples are for illustrative purposes only and are not intended to limit the invention. Those of ordinary skill in the art will readily recognize parameters that can be changed or modified to yield essentially the same results.

Example 1

In Example 1, a steam cracking furnace was modeled using molecular kinetics (phenomenological model) and radical kinetics based software (detailed model). The phenomenological model lumped all hydrocarbon above C$_5$ as benzene to reduce the computational time. The range of input operating conditions is illustrated below in Table 1 and Table 2.

TABLE 1

| Operating Range | COT, °C. | HC FLOW, tph | COP, bar | S/O RATIO |
|---|---|---|---|---|
| Max | 869.9552 | 59.9664 | 2.1000 | 0.4498 |
| Min | 820.0432 | 40.0208 | 1.7005 | 0.2501 |

TABLE 2

| | | | Mass-fraction | | |
|---|---|---|---|---|---|
| Methane | Ethane | Propane | N—$C_4H_{10}$ | Ethylene | Propylene |
| 0.3444 | 0.9469 | 0.9471 | 0.2824 | 0.3537 | 0.2093 |
| 0.0000 | 0.0001 | 0.0000 | 0.0000 | 0.0000 | 0.0000 |

Figure 4:
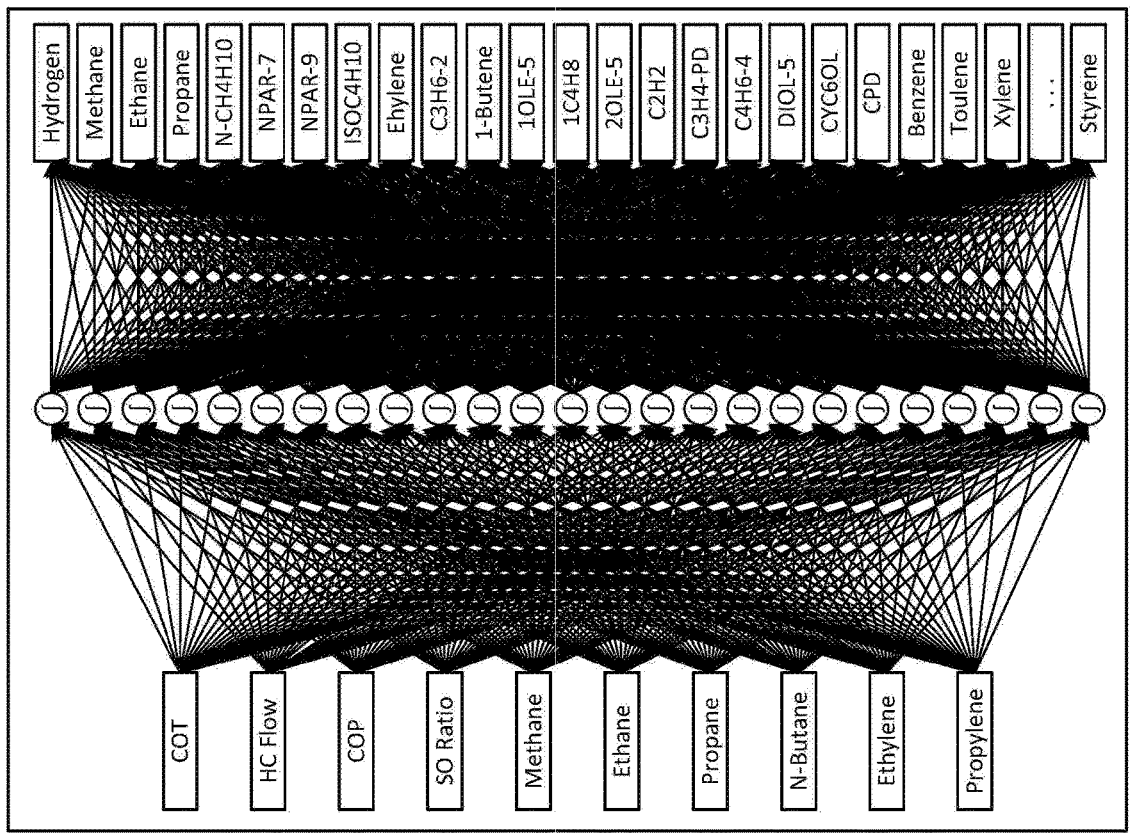
FIG. 4 is a diagram illustrating an exemplary neural network model for predicting a difference in yields based on modelling data according to embodiments.

A space filling DOE design was then used to generate the required inputs for the training dataset (1000 data points). Once the training dataset was generated using the models, the difference between the yield predictions of two models was calculated, as described above with respect to FIG. 2, and was used to train the machine learning tool (e.g. Neural networks), as described above with respect to FIG. 3. Referring to FIG. 4, a diagram illustrating an exemplary neural network model for predicting a difference in yields based on modelling data according to embodiments is shown. The neural network model of FIG. 4 was generated with the input conditions given in Tables 1 and 2. As shown in FIG. 4, Yields for components which were lumped in the phenomenological model can now be predicted using this hybrid approach of embodiments.

Figure 5:
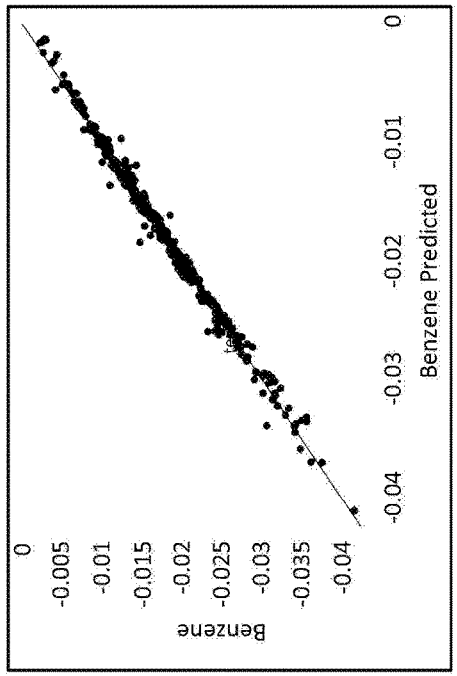
FIG. 5 is a diagram illustrating a plot comparing a predicted yield of benzene determined according to embodiments and an actual benzene yield.

Referring to FIG. 5, a diagram illustrating a plot comparing a predicted yield of benzene determined according to embodiments and an actual benzene yield is shown. In an embodiment, the plot of FIG. 5 may correspond to neural network training validation results for ε(benzene). The final benzene yield prediction derived by the hybrid modelling technique may be given by:

$$y_{benzene} = y_{phenomenological_{benzene}} + \varepsilon(benzene), \quad \text{Eq. 1}$$

Figure 6:
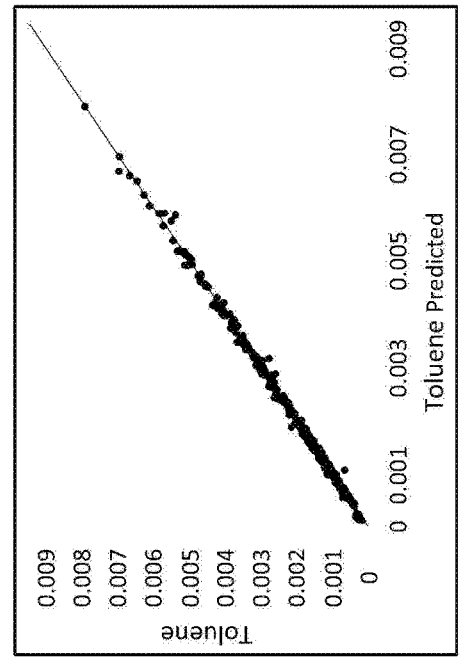
FIG. 6 is a diagram illustrating a plot comparing a predicted yield of toluene determined according to embodiments and an actual toluene yield.

FIG. 6 is a diagram illustrating a plot comparing a predicted yield of toluene determined according to embodiments and an actual toluene yield is shown. In an embodiment, the plot of FIG. 6 may correspond to neural network training validation results for ε(Toluene). In an embodiment, when evaluating the phenomenological model, toluene may be lumped in with benzene as a single component to reduce computational time. However, with the hybrid modelling technique of embodiments, toluene can be delumped and calculated as:

$$y_{toluene} = \varepsilon(toluene), \quad \text{Eq. 2}$$

As the phenomenological model and the neural network model both requires less computational time, using both of them under the hybrid modelling technique of embodiments allows optimization of a complete plant model in a significantly less amount of time. For example, in Table 3, below, a comparison of computational time for whole plant simulation/optimization is provided.

TABLE 3

| | Hybrid Approach | Detailed Radical kinetics based model |
|---|---|---|
| Single whole plant Simulation, with connected recycles | 1 minute | 5 minutes |
| Whole plant optimization | 2 minutes | 4-5 hours |

As shown in Table 3 above, when utilizing the hybrid modelling technique of embodiments, it is possible to carry optimization in Equation oriented mode, resulting in very quick solution. Stated another way, the hybrid modelling technique of embodiments models the olefin plant as a series of equations and variables representative of the olefin plant's operations, where the series of equations and variables can be solved simultaneously, enabling simulation results (e.g., the corrected Yield 330 of FIG. 3) to be obtained more quickly.

Additionally, as explained above, when the input conditions are outside the training range (Tables 1 and 2), the output may be obtained from the phenomenological model. This increases the robustness provided by the hybrid modelling technique of embodiments, and gives the hybrid approach an advantage over existing stand-alone machine learning based tools. Using the above training set data, both a hybrid model and stand-alone neural network model were generated. The results of the models for data points outside the training region are compared in Table 4.

TABLE 4

| | | | Output Comparison | | |
|---|---|---|---|---|---|
| Input Conditions | | Mass Fraction | Hybrid | Stand-Alone | Detailed |
| COT | 850 C. | HYDROGEN | 0.040 | 0.036 | 0.041 |
| HC FLOW | 40 tph | METHANE | 0.060 | 0.084 | 0.059 |
| COP | 2 bar | ETHANE | 0.314 | 0.367 | 0.306 |
| SO RATIO | 0.3 | PROPANE | 0.001 | −0.047 | 0.002 |
| Methane | 0 | ETHYLENE | 0.543 | 0.562 | 0.538 |
| Ethane | 1 | $C_3H_6^{-2}$ | 0.006 | −0.034 | 0.010 |
| Propane | 0 | $C_2H_2$ | 0.005 | 0.004 | 0.005 |
| N-Butane | 0 | $C_4H_6^{-4}$ | 0.016 | 0.017 | 0.017 |
| Ethylene | 0 | BENZENE | 0.003 | 0.008 | 0.008 |
| Propylene | 0 | | | | |

It is clear from the results that hybrid approach closely resembles the detailed radical kinetics model result whereas stand-alone neural network model deviates and also results in unrealistic negative mass fraction for some components.

Although embodiments of the present invention have been described with reference to blocks of FIGS. 1-3 and 7, it should be appreciated that operation of the present invention is not limited to the particular blocks and/or the particular order of the blocks illustrated in FIGS. 1-3 and 7. Accordingly, embodiments of the invention may provide functionality as described herein using various blocks in a sequence different than that of FIGS. 1-3 and 7.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of producing olefins by an olefins plant, the method comprising:
    running a phenomenological model, with input including operating conditions for a cracking unit, to generate an output of a first olefin yield of the cracking unit, the phenomenological model based on molecular kinetics;

running a free radical kinetics based model, with input including the operating conditions for the cracking unit, to generate an output of a second olefin yield of the cracking unit;

determining the difference between the first olefin yield of the cracking unit and the second olefin yield of the cracking unit (E);

running a machine learning model, with input including the operating conditions for the cracking unit, to generate a predicted E;

adding the predicted E to the first olefin yield to obtain a corrected olefin yield;

establishing new operating conditions for the cracking unit and/or the olefin plant based at least on the corrected olefin yield; and producing the olefins by the olefin plant while operating under the new operating conditions.

2. The method of claim 1, wherein the producing the olefins by the olefin plant while operating under the new operating conditions comprises steam cracking.

3. The method of claim 1, wherein the olefins comprise ethylene.

4. The method of claim 1, wherein the method comprises generating training data based on the phenomenological model and the free radical kinetics based model.

5. The method of claim 1, wherein the method comprises receiving plant data, wherein the plant data is utilized to run the free radical kinetics based model.

6. The method of claim 5, wherein the plant data comprises data representative of actual operating conditions and data representative of actual olefin yields observed based on the actual operating conditions, the data representative of the actual operating conditions comprising data associated with a feed flow rate, a feed flow composition, a temperature, and a pressure utilized to produce the olefins.

7. The method of claim 1, wherein the method comprises utilizing stochastic tools, wherein the stochastic tools include at least Kalman filters.

8. A non-transitory computer-readable storage medium storing instructions that, when executed by one or more processors, cause the one or more processors to perform operations for analyzing, controlling, or both, production of olefins by an olefins plant, the operations comprising:

running a phenomenological model, with input including operating conditions for a cracking unit, to generate an output of a first olefin yield of the cracking unit, the phenomenological model based on molecular kinetics, the operating conditions comprising conditions selected from the list consisting of: feed flow rate, feed flow composition, temperature, pressure, and combinations thereof;

running a free radical kinetics based model, with input including the operating conditions for the cracking unit, to generate an output of a second olefin yield of the cracking unit;

determining the difference between the first olefin yield of the cracking unit and the second olefin yield of the cracking unit (E);

running a machine learning model, with input including the operating conditions for the cracking unit, to generate a predicted E;

adding the predicted E to the first olefin yield to obtain a corrected olefin yield;

establishing new operating conditions for the cracking unit and/or the olefin plant based at least on the corrected olefin yield; and producing the olefins by the olefin plant while operating under the new operating conditions.

9. The non-transitory computer-readable storage medium of claim 8, wherein the producing the olefins by the olefin plant while operating under the new operating conditions comprises steam cracking.

10. The non-transitory computer-readable storage medium of claim 8, wherein the olefins comprise ethylene.

11. The non-transitory computer-readable storage medium of claim 8, wherein the operations include generating training data based on the phenomenological model and the free radical kinetics based model.

12. The non-transitory computer-readable storage medium of claim 8, wherein the operations include receiving plant data, wherein the plant data is utilized to run the free radical kinetics based model.

13. The non-transitory computer-readable storage medium of claim 12, wherein the plant data comprises data representative of actual operating conditions and data representative of actual olefin yields observed based on the actual operating conditions, the data representative of the actual operating conditions comprising data associated with a feed flow rate, a feed flow composition, a temperature, and a pressure utilized to produce the olefins.

14. The non-transitory computer-readable storage medium of claim 8, wherein the operations include utilizing stochastic tools, wherein the stochastic tools include at least Kalman filters.

15. A system for producing olefins at an olefins plant, the system comprising:

at least one processor configured to:

run a phenomenological model, with input including operating conditions for a cracking unit, to generate an output of a first olefin yield of the cracking unit, the phenomenological model based on molecular kinetics, the operating conditions comprising conditions selected from the list consisting of: feed flow rate, feed flow composition, temperature, pressure, and combinations thereof;

run a free radical kinetics based model, with input including the operating conditions for the cracking unit, to generate an output of a second olefin yield of the cracking unit;

determine the difference between the first olefin yield of the cracking unit and the second olefin yield of the cracking unit (E);

run a machine learning model, with input including the operating conditions for the cracking unit, to generate a predicted E, wherein the running of the machine learning model comprises training the machine learning model with training data comprising a predetermined range of operating conditions;

add the predicted E to the first olefin yield to obtain a corrected olefin yield;

establish new operating conditions for the cracking unit and/or the olefin plant based at least on the corrected olefin yield; and initiate operations to produce the olefins by the olefin plant while operating under the new operating conditions; and a memory coupled to the at least one processor.

16. The system of claim 15, wherein the production of the olefins by the olefin plant while operating under the new operating conditions comprises steam cracking.

17. The system of claim 15, wherein the olefins comprise ethylene.

18. The system of claim 15, wherein the at least one processor is further configured to generate training data based on the phenomenological model and the free radical kinetics based model.

19. The system of claim 15, wherein the at least one processor is further configured to receive plant data and utilize the plan data to run the free radical kinetics based model.

20. The system of claim 19, wherein the plant data comprises data representative of actual operating conditions and data representative of actual olefin yields observed based on the actual operating conditions, the data representative of the actual operating conditions comprising data associated with a feed flow rate, a feed flow composition, a temperature, and a pressure utilized to produce the olefins.

* * * * *